United States Patent [19]

Uriss

[11] Patent Number: 4,574,823
[45] Date of Patent: Mar. 11, 1986

[54] DENTAL FLOSS INSTRUMENT

[76] Inventor: Michael B. Uriss, 3516 - 170th Ct., Hammond, Ind. 46323

[21] Appl. No.: 494,803

[22] Filed: May 16, 1983

[51] Int. Cl.4 .............................................. A61C 15/00
[52] U.S. Cl. ................................................. 132/92 R
[58] Field of Search ..................................... 132/92 R

[56] References Cited

U.S. PATENT DOCUMENTS

| 2,554,526 | 5/1951 | Dembenski | 132/92 R |
| 3,534,745 | 10/1970 | Waters | 132/92 R |
| 4,178,947 | 12/1979 | McCourry | 132/92 R |
| 4,214,598 | 7/1980 | Lee | 132/92 R |

Primary Examiner—Gregory E. McNeill
Attorney, Agent, or Firm—Albert L. Jeffers; Stephen T. Belsheim

[57] ABSTRACT

This invention is a dental instrument for flossing teeth. It is formed from a suitable thermoplastic material which may be molded in the shape of a circular container provided with a tangentially or radially extending shaft member for supporting a part of the floss filament longitudinally taut at the looped end of the shaft member. The perimeter of the circular container is provided with a pawl lever as an integral part of the perimeter. The dental floss is provided wrapped on a spool which has a rim circumferentially notched, forming teeth which are engaged by the pawl lever.

13 Claims, 8 Drawing Figures

DENTAL FLOSS INSTRUMENT

BACKGROUND OF THE INVENTION

1. Field of the Invention

This invention relates generally to dental instruments and more particularly to a dental floss dispenser holder.

2. Description of the Prior Art

Dental floss devices of the prior art that I am aware of for performing the dual function of dispensing dental floss and holding a portion of the dental floss taut and manipulable to clean teeth are relatively expensive to manufacture and complicated to operate. These prior art dental floss instruments are expensive to manufacture because they are complicated in structure. They are generally comprised of numerous individual parts requiring assembly to form the completed instrument in order to function as a dental floss holder, dispenser and manipulator.

SUMMARY OF THE INVENTION

I have invented a floss dispenser holder which is easy and inexpensive to manufacture, having a minimum of separate parts requiring assembly. I form the floss holder of this invention from a suitable thermoplastic material which may be molded in the shape of an open end circular container provided with a tangentially or radially extending shaft member for supporting a part of the floss filament longitudinally taut at the distal end of the shaft member. The perimeter of the circular container is provided with a pawl lever as an integral part of the perimeter having been formed from the same forming material at the same time. The dental floss is provided wrapped on a spool which has a rim circumferentially notched, forming teeth which are engaged by the pawl lever. A circular cap is formed with a circumferential shoulder to engage the edge of the container perimeter which serves as a protective cover.

Other objects and advantages of this invention will become more apparent upon a closer study of the following description of this invention taken with reference to the accompanying drawing which illustrates a preferred embodiment of my invention.

DETAILED DESCRIPTION OF THE INVENTION

Figure 1:
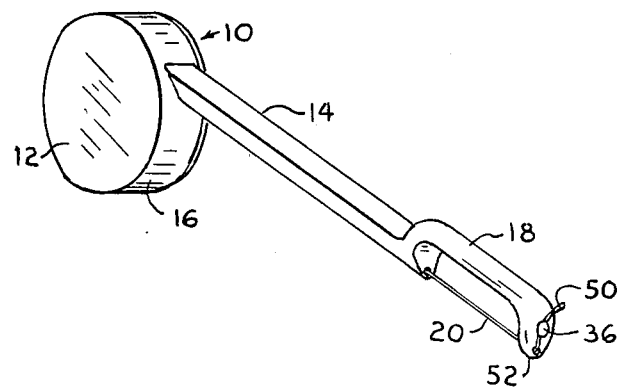
FIG. 1 is a perspective view of the floss dental instrument of this invention.
Figure 2:
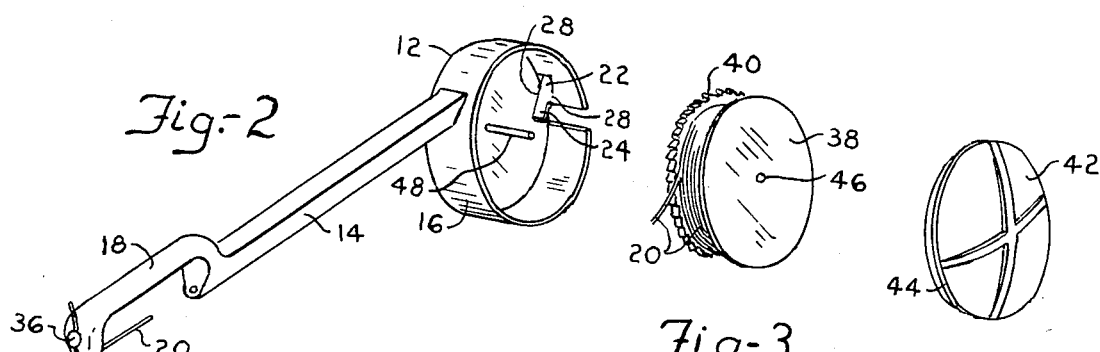
FIG. 2 is another perspective view thereof.
Figure 3:
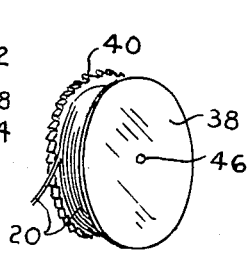
FIG. 3 is a perspective view of the floss spool which is assembled to the side of the instrument shown in FIG. 2.
Figure 4:
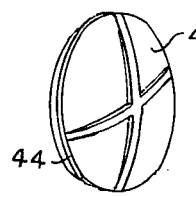
FIG. 4 is a perspective view of the cap which is assembled to the side of the instrument shown in FIG. 2.
Figure 5:
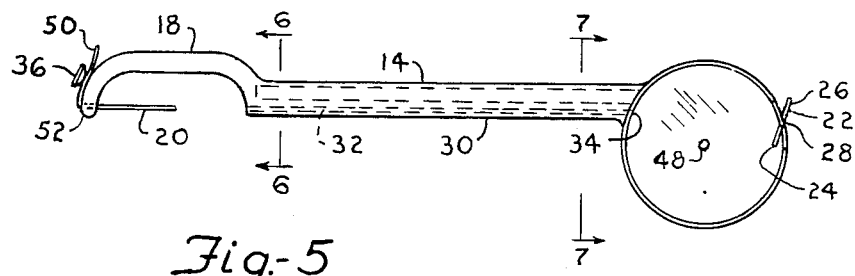
FIG. 5 is a side elevation of this invention with the spool and cap removed.
Figure 6:
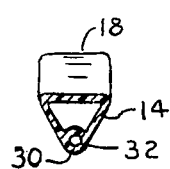
FIG. 6 is a cross-sectional view taken along lines 6—6 of FIG. 5.
Figure 7:
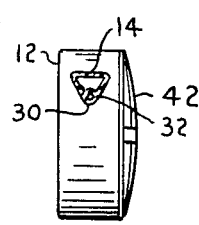
FIG. 7 is a sectional view taken along lines 7—7 of FIG. 5.
Figure 8:
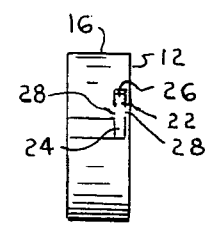
FIG. 8 is an end view taken from the right side of FIG. 5.

Referring now more particularly to the drawings, numeral 10 designates generally the dental floss dispenser holder embodying my invention. It comprises a integrally molded unit formed as a shallow open ended circular container 12 provided with an extended shaft member 14. Shaft member 14 is rectilinear a major part thereof and extends generally tangentially or radially from perimeter 16 of container 12. Adjacent its distal end, shaft member 14 is formed with a loop or recessed part 18 to provide teeth working space between the floss 20 and part 18 of shaft member 14. I prefer to form shaft member 14 with a triangular cross-sectional shape to provide maximum longitudinal rigidity and minimum width and depth so that member 14 may be easily manipulated around a persons teeth. Part of perimeter 16 of container 12 is formed with an integrally formed appending pawl lever 22. Pawl lever 22 is formed from the same plastic forming material as container 12, being an integral part of perimeter 16 at approximately the center part of lever 22. Pawl lever 22 is generally rectilinear and is molded to be positioned diagonally relative to perimeter 16 so that end 26 thereof extends interior of the container and the other end 26 thereof extends exterior of the container. The thermoplastic forming material selected should have sufficient rigidity to maintain its over all shape, sufficiently elastic so that pawl lever 22, as an appendage to perimeter 16, may be pivotally flexed at its point of juncture 28 and sufficiently tough to withstand repeated flexing of juncture 28 without rupture. Plastic forming material having the physical characteristics above described are well known to those skilled in the art of plastic materials and are commercially available. For example, a polypropylene plastic material may be satisfactorily used as forming material, however any number of materials will be satisfactory.

Formed along or adjacent longitudinal edge 30 of triangular shaped shaft member 14 is a passageway 32 the length thereof which communicates with the interior of container 12 by means of hole 34 in perimeter 16. Hole 34 is in registration with passageway 32 and receives therethrough floss filament 20. Floss filament 20 is contained in passageway 32, the end of which tautly spans recessed loop part 18 of shaft member 14 and is secured by wrapping friction to a capstan type lug 36 molded on the distal end thereof.

It is contemplated that dental floss 20 of my invention be provided on a spool 38. One end of spool 38 is formed with a circular rim having ratchet teeth 40 therearound. Spool 38 and ratchet teeth 40 are diametrally dimensioned to concentrically fit in container 12 and rotatable therein when the other end 26 of pawl lever 22 is depressed to pivot lever 22 serving to disengage end 24 of pawl lever 22 from teeth 40. When other end 26 of pawl lever 22 is released, the inherent resiliency of the material forming the connecting juncture 28 between lever 22 and perimeter 16 will cause pawl lever 22 to assume its diagonal position thereby engaging ratchet teeth 40 of spool 38 preventing further rotation thereof. With the other end of filament 20 securely anchored to lug 36 having been previously tightly stretched while end 24 of pawl lever 20 was engaged to ratchet teeth 16, a taut floss filament portion spanning recessed part 18 of shaft member 14 is provided. I provide a cap 42 which is formed with a circumferential shouldered edge 44 to snap on the edge of perimeter 16 to protectively cover floss spool 38. Spool 38 may be formed with a center hole 46 to be mounted on a center pin 48 provided in container 12; however, spool 38 may operate satisfactory without being mounted on pin 48 and therefore pin 48 may be eliminated if desired.

Having formed the floss dispenser holder 10 including pawl lever 22 as a unitary article from a thermoplastic material as above described, spool 38 formed with ratchet teeth 40 around the rim of one end thereof and containing dental floss filament 20 is deposited in container 12 so that ratchet teeth 40 is aligned with end 24 of pawl lever 22. Lead end 50 of floss filament 20 is inserted through hole 34 in perimeter 16 and guided along passageway 32 in longitudinal edge 30 of shaft member 14. It is then inserted through a hole in distal end 52 longitudinally spanning the space between the rectlinear part of shaft member 14 and the said distal end 54. It is then secured by wrapping the lead end 50 around lug 36. As described above lug 36 is capstan type, meaning that the shaft part is cone-shaped to provide an acute angle at its juncture with the shaft member so that the floss end wrapped therearound will be wedged at the juncture and thereby fictionally held in place while at the same time it may be easily released by unwrapping from lug 36 for removing the used portion of floss filament 20 and positioning a new portion of the floss filament in place. During the floss inserting operation, the other end part 26 of pawl lever 22 is depressed so that end part 24 thereof is disengaged from ratchet teeth 40 of spool 38 allowing spool 38 to rotate and dispense floss filament 20 as required. During the floss tightening operation, other end part 26 of lever 22 is released so that lever 22 springs back to its normal diagonal position engaging ratchet teeth 40 of spool 38 with end part 24 thereof preventing further rotation of spool 38 and thereby locking it in place. With spool 38 locked in place and pulling the floss filament to a tautness desired, the end is then secured to and frictionally anchored on capstan lug 36. Excess length of lead end 50 of floss filament 20 may be broken by a sharp pull which operates to break the filament and further wedge the filament end around lug 36.

I claim:

1. A device for dispensing and holding dental floss comprising:
   a container having a circular perimeter, said perimeter having an aperture and a hole therein;
   a lever member in said aperture, one end of said lever member extending interior of said container, and the other end of said lever member extending exterior of said container;
   a pivot member connecting said lever and said perimeter of said container, said pivot member being flexible for allowing said lever member to pivot relative to said container;
   an elongated member extending from said perimeter of said container, said elongated member adjacent the distal end thereof being looped to provide a space longitudinally therebetween; and
   a spool having a rim, said spool being concentrically positioned in said container so that said rim of said spool is aligned with said one end of said lever, said pivot movement of said lever engaging and disengaging said rim to selectively permit rotation of said spool.

2. The device of claim 1 wherein said perimeter of said container, lever member and pivot member are further characterized as being integrally formed from a common thermoplastic material.

3. The device of claim 1 wherein said elongated member is further characterized as being provided with a longitudinal groove the length thereof.

4. The device of claim 3 wherein said hole in said perimeter is further characterized as being in registration with said groove in said elongated member.

5. The device of claim 1 wherein said rim of said spool is further characterized by being provided with teeth circumferentially therearound and said one end of said lever being engageable with said teeth.

6. A device for dispensing and holding dental floss comprising:
   a container having a circular perimeter, said perimeter having an aperture and a hole therein;
   a lever member in said aperture, one end of said lever member extending interior of said container, and the other end of said lever member extending exterior of said container;
   a pivot member connecting said lever and said perimeter of said container, said pivot member being flexible for allowing said lever member to pivot relative to said container;
   an elongated member extending from said perimeter of said container, said elongated member adjacent the distal end thereof being looped to provide a space longitudinally therebetween;
   a spool having a rim, said spool being concentrically positioned in said container so that said rim of said spool is aligned with said one end of said lever, said pivot movement of said lever engaging and disengaging said rim to selectively permit rotation of said spool; and
   dental floss filament on said spool, said dental floss filament extends through said hole in said perimeter of said container, extending along said elongated member spanning said longitudinal space and secured to said distal end.

7. The device of claim 6 wherein said perimeter of said container, lever member and pivot member are further characterized as being integrally formed from a common thermoplastic material.

8. The device of claim 6 wherein said elongated member is further characterized as being provided with a longitudinal groove the length thereof.

9. The device of claim 8 wherein said hole in said perimeter is further characterized as being in registration with said groove in said elongated member.

10. The device of claim 6 wherein said rim of said spool is further characterized as being provided with teeth circumferentially therearound and said one end of said lever being engageable with said teeth.

11. A device for dispensing and holding dental floss comprising:
    a container having a circular perimeter, said perimeter having an aperture and a hole therein;
    a lever member in said aperture, one end of said lever member extending interior of said container, and the other end of said lever member extending exterior of said container;
    a pivot member connecting said lever and said perimeter of said container, said pivot member being flexible for allowing said lever member to pivot relative to said container;
    an elongated member extending from said perimeter of said container, said elongated member adjacent the distal end thereof including a C-shaped portion to define a longitudinal space;
    a spool having a rim, said spool being concentrically positioned in said container so that said rim of said spool is aligned with said one end of said lever, said pivot movement of said lever engaging and disengaging said rim to selectively permit rotation of said spool; and dental floss filament on said spool, said dental floss filament extends through said hole in said perimeter of said container and along said elongated member spanning the longitudinal space and secured to said distal end.

12. The device of claim 11 wherein the portion of the filament extending from the distal end of the elongated member to the spool is generally straight.

13. The device of claim 11 wherein the portion of the filament spanning the longitudinal space is generally parallel to the longitudinal axis of said elongated member.

* * * * *